(12) United States Patent
Janousek et al.

(10) Patent No.: US 11,633,492 B2
(45) Date of Patent: Apr. 25, 2023

(54) PROCESS FOR THE SYNTHESIS OF LINKER-DRUG VC-SECO-DUBA

(71) Applicant: BYONDIS B.V., Nijmegen (NL)

(72) Inventors: Vladimir Janousek, Bechovice (CZ); Martin Kas, Bechovice (CZ)

(73) Assignee: Byondis B.V., Nijmegen (NL)

( * ) Notice: Subject to any disclaimer, the term of this patent is extended or adjusted under 35 U.S.C. 154(b) by 208 days.

(21) Appl. No.: 16/766,150

(22) PCT Filed: Nov. 22, 2018

(86) PCT No.: PCT/EP2018/082199
§ 371 (c)(1),
(2) Date: May 21, 2020

(87) PCT Pub. No.: WO2019/101850
PCT Pub. Date: May 31, 2019

(65) Prior Publication Data
US 2020/0368362 A1    Nov. 26, 2020

(30) Foreign Application Priority Data

Nov. 24, 2017 (EP) .................................... 17203457

(51) Int. Cl.
| C07D 471/04 | (2006.01) |
| A61K 47/68 | (2017.01) |
| A61K 31/437 | (2006.01) |
| A61K 39/395 | (2006.01) |

(52) U.S. Cl.
CPC ........ A61K 47/6803 (2017.08); A61K 31/437 (2013.01); A61K 39/3955 (2013.01); C07D 471/04 (2013.01)

(58) Field of Classification Search
CPC .................................................. C07D 471/04
USPC ........................................................ 546/121
See application file for complete search history.

(56) References Cited

FOREIGN PATENT DOCUMENTS

| WO | WO 2011/133039 A2 | 10/2011 |
| WO | WO 2015/177360 A1 | 11/2015 |
| WO | WO 2015/185142 A1 | 12/2015 |
| WO | WO 2017/137628 A1 | 8/2017 |

OTHER PUBLICATIONS

M.M.C. Van Der Lee et al, "The Preclinical Profile of the Duocarmycin-Based HER2-Targeting ADC SYD985 Predicts for Clinical Benefit in Low HER2-Expressing Breast Cancers" *Molecular Cancer Therapeutics*, Jan. 14, 2015, vol. 14, No. 3, pp. 692-703.

J. Black et al., "SYD985, a Novel Duocarmycin-Based HER2-Targeting Antibody-Drug Conjugate, Shows Antitumor Activity in Uterine Serous Carcinoma with HER2/Neu Expression" *Molecular Cancer Therapeutics*, Jun. 2, 2016, vol. 15, No. 8, pp. 1900-1909.

Ronald C. Elgersma et al, "Design, Synthesis, and Evaluation of Linker-Duocarmycin Payloads: Toward Selection of HER2-Targeting Antibody-Drug Conjugate SYD985", *Molecular Pharmaceutics*, vol. 12, No. 6, Jun. 1, 2015, pp. 1813-1835.

W. Dokter et al, "Preclinical Profile of the HER2-Targeting ADC SYD983/SYD985: Introduction of a New Duocarmycin-Based Linker-Drug Platform", *Molecular Cancer Therapeutics*, vol. 13, No. 11, Sep. 4, 2014, pp. 2618-2629.

*Primary Examiner* — Douglas M Willis
(74) *Attorney, Agent, or Firm* — Buscher Patent PLLC

(57) ABSTRACT

The compound of formula (II) is an advantageous intermediate for improving the process of synthesizing the linker-drug vc-seco-DUBA, as well as for the overall process for preparing an antibody-drug conjugate comprising the vc-seco-DUBA linker-drug. The methods of making the compound of formula (II) can include recovery of the compound as a solid, such as via crystallization, in high yields and purity.

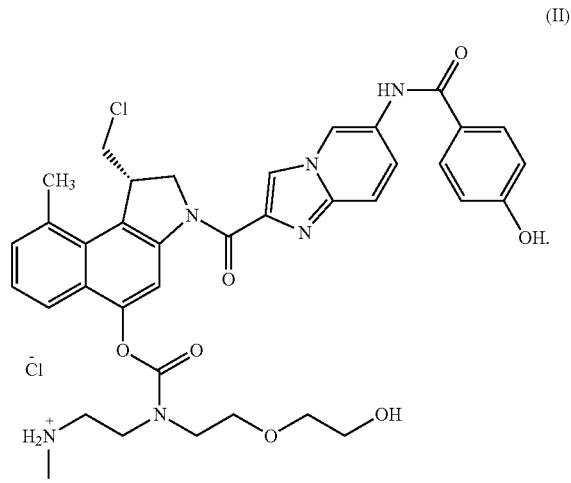

16 Claims, No Drawings

PROCESS FOR THE SYNTHESIS OF LINKER-DRUG VC-SECO-DUBA

FIELD OF THE INVENTION

The present invention relates to an improved process for the synthesis of linker-drug vc-seco-DUBA and its intermediates, as well as to the use of said improved process in a process for preparing an antibody-drug conjugate comprising the vc-seco-DUBA linker-drug.

BACKGROUND OF THE PRESENT INVENTION

Duocarmycins are members of a family of antitumour antibiotics that include duocarmycin A, duocarmycin SA, and CC-1065. They are known for their potent antitumour properties, but are normally not used on their own because of their extremely high toxicity. Currently, duocarmycins are being explored as cytotoxic drugs in antibody-drug conjugates (ADCs).

ADCs have the potential to address the great unmet need for effective new treatments in cancer by directing the highly potent cytotoxic drug specifically to cancer cells, thereby enhancing efficacy while reducing the potential systemic toxic side effects of the small molecule drug.

One of the key aspects for the future commercial success of ADCs is a process for the synthesis of the cytotoxic drug and the corresponding linker-drug construct, in which a linker moiety is attached to the cytotoxic drug in order to facilitate conjugation to the antibody, which process is suitable for production on an industrial scale.

Linker-drug vc-seco-DUBA of formula (I) first disclosed in WO2011/133039 as compound 18b on p. 210, 11. 21-27, is an example of a highly potent CC-1065 analog. The ADC of vc-seco-DUBA with the anti-HER2 antibody trastuzumab, i.e. SYD985 or (vic-)trastuzumab duocarmazine, was used successfully in several preclinical studies (M.M.C. van der Lee et al., Molecular Cancer Therapeutics, 2015, 14(3), 692-703; J. Black et al., Molecular Cancer Therapeutics, 2016, 15 (8), 1900-1909) and Phase I clinical trials (ClinicalTrials.gov NCT02277717). Currently, SYD985 treatment is compared directly with treatment of physician's choice in a Phase III clinical trial in patients with HER2-positive locally advanced or metastatic breast cancer (TULIP; ClinicalTrials.gov NCT03262935).

The synthesis of the linker-drug vc-seco-DUBA is described in WO2011/133039 as a four-step process. Preparation of vc-seco-DUBA following this process on a 50-100 mg laboratory scale provided the linker-drug with an overall yield of only 21-25%. The latter two steps, i.e. steps 3 and 4, of this process are crucial for the overall yield of vc-seco-DUBA from the total process, showing a combined yield of only about 50%. On an industrial scale the yield of this four-step process will be even lower.

Hence, there is a need for an improved process for preparing vc-seco-DUBA. In particular, there is a need for a process which is efficient in terms of yield and chemical purity, cost effective in terms of reagents and reaction conditions, and which is suitable for production on an industrial scale.

BRIEF DESCRIPTION OF THE PRESENT INVENTION

The present invention relates to an improved process for the synthesis of linker-drug vc-seco-DUBA and its interme-

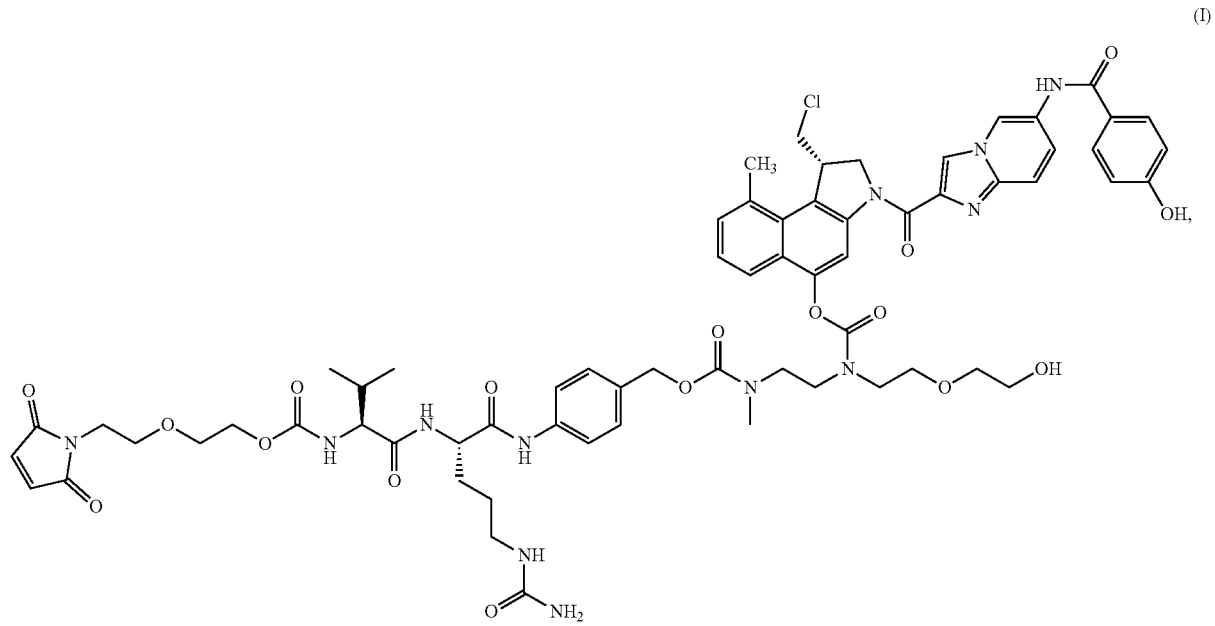 [SMILES: Cc1cccc2c(OC(=O)N(CCOCCO)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cn2cc(NC(=O)c3ccc(O)cc3)ccc2n1]

diates with process conditions that are suitable for production on an industrial scale, and which provides the desired vc-seco-DUBA product in an improved yield.

In a first aspect, the present invention relates to a compound of formula (II)

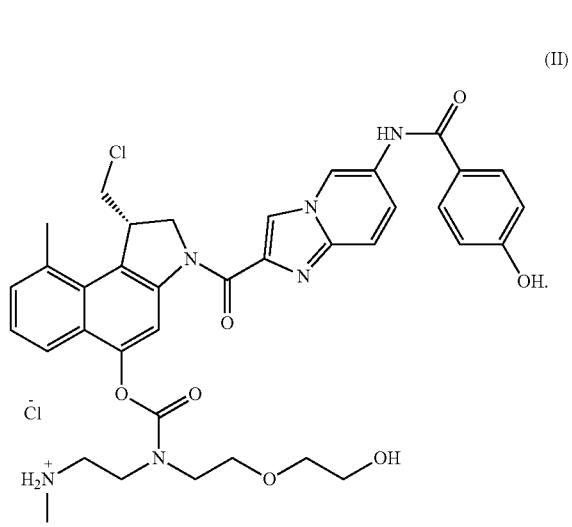 [SMILES: CNCCN(CCOCCO)C(=O)Oc1cc2c(c3c(C)cccc13)[C@H](CCl)CN2C(=O)c1cn2cc(NC(=O)c3ccc(O)cc3)ccc2n1 ; Cl]

(II)

In a second aspect, the invention provides for a process comprising reacting a compound of formula (III)

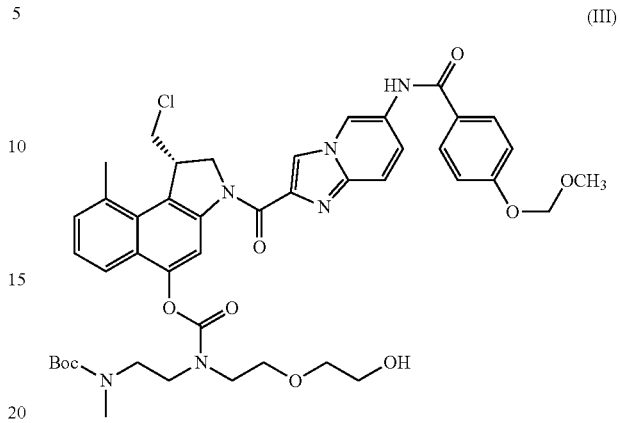

(III)

with hydrogen chloride in 1,4-dioxane to form a compound of formula (II).

In a third aspect, the invention relates to the use of a compound of formula (II) in a process for making vc-seco-DUBA of formula (I)

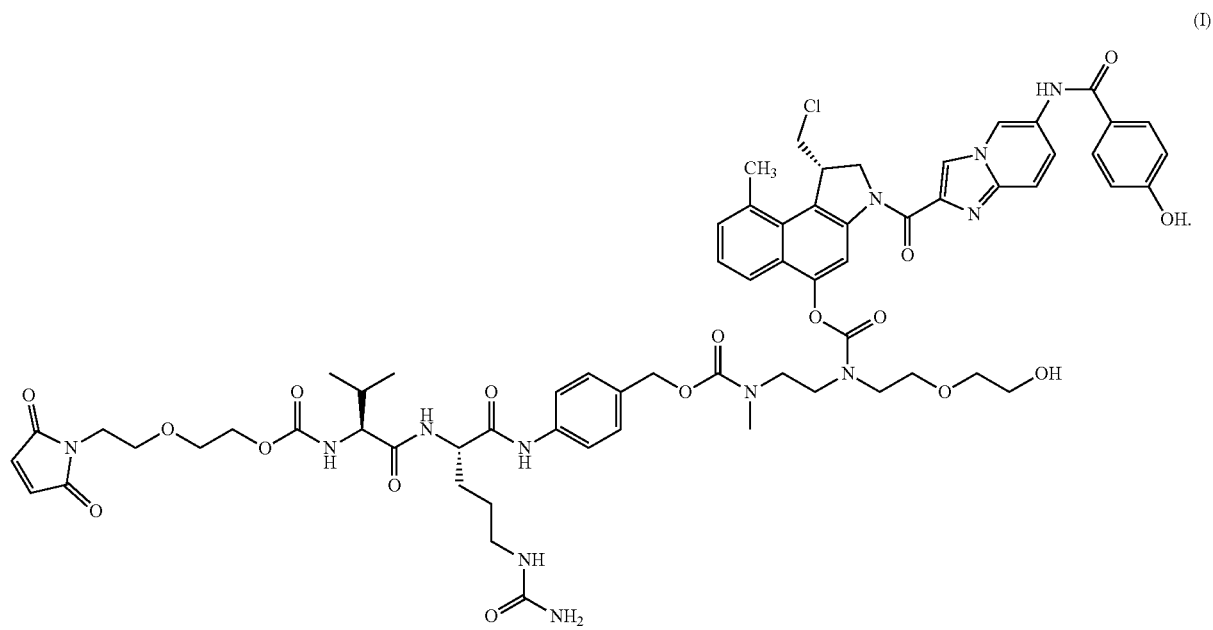 [SMILES: Cc1cccc2c(OC(=O)N(CCOCCO)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cn2cc(NC(=O)c3ccc(O)cc3)ccc2n1]

(I)

In a fourth aspect, the invention relates to the use of the process for making vc-seco-DUBA in a process for making a vc-seco-DUBA-containing antibody-drug conjugate.

DETAILED DESCRIPTION OF THE PRESENT INVENTION

Duocarmycins are a class of structurally-related toxins first isolated from a culture broth of *Streptomyces* species. They are members of a family of antitumour antibiotics that include duocarmycin A, duocarmycin SA, and CC-1065. Duocarmycins bind to the minor groove of DNA and subsequently cause irreversible alkylation of DNA. This disrupts the nucleic acid architecture, which eventually leads to tumour cell death.

WO2011/133039 specifically discloses the highly potent linker-drug vc-seco-DUBA of formula (I) (compound 18b on p. 210, ll. 21-27) which comprises a duocarmycin derivative of CC-1065

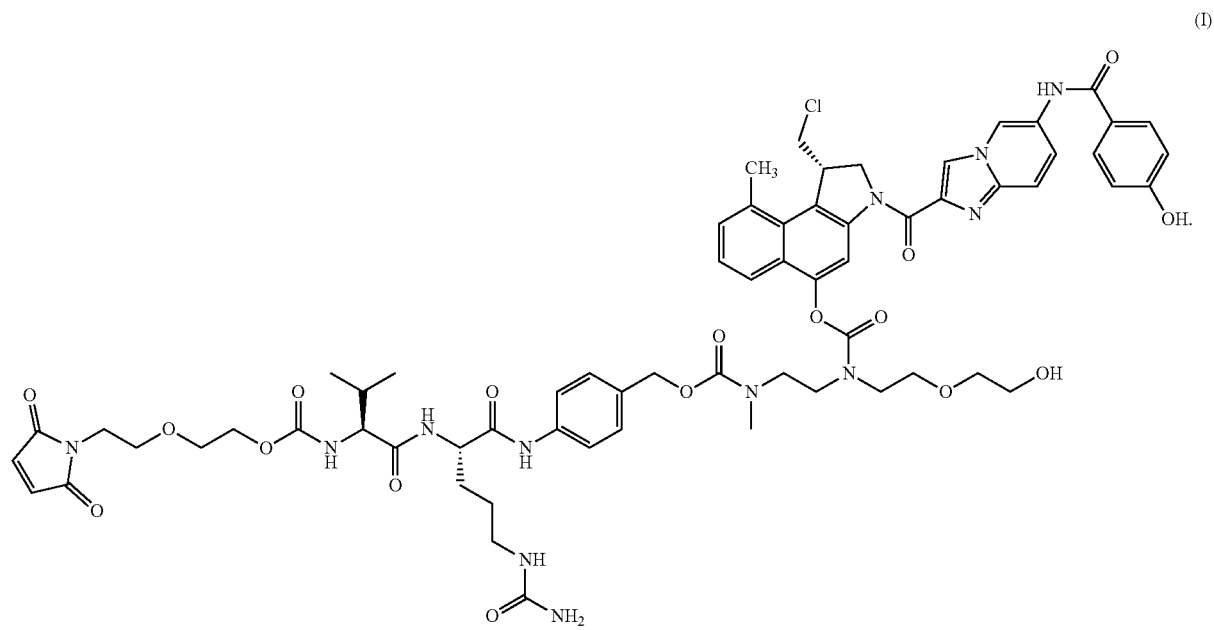 [SMILES: Cc1cccc2c(OC(=O)N(CCOCCO)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cn2cc(NC(=O)c3ccc(O)cc3)ccc2n1]

(I)

The present invention relates to an improved process for the production of vc-seco-DUBA with a surprisingly high yield and which can be successfully applied on an industrial scale.

The chemical synthesis of the vc-seco-DUBA linker-drug in Example 10 of WO2011/133039 is described as a four-step process

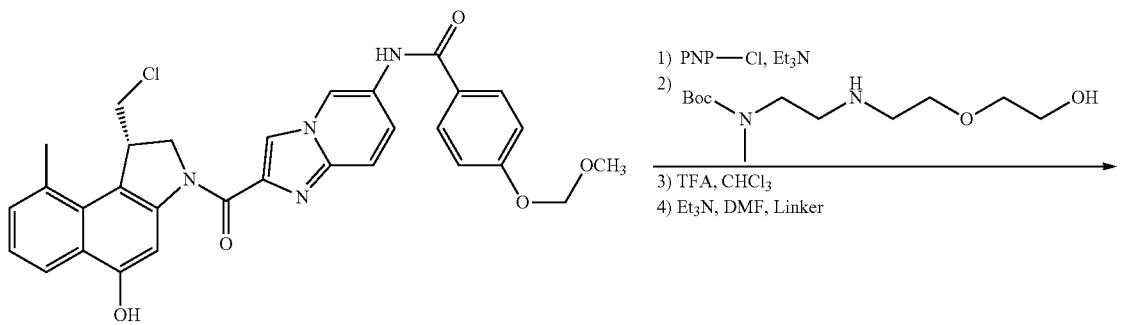

-continued

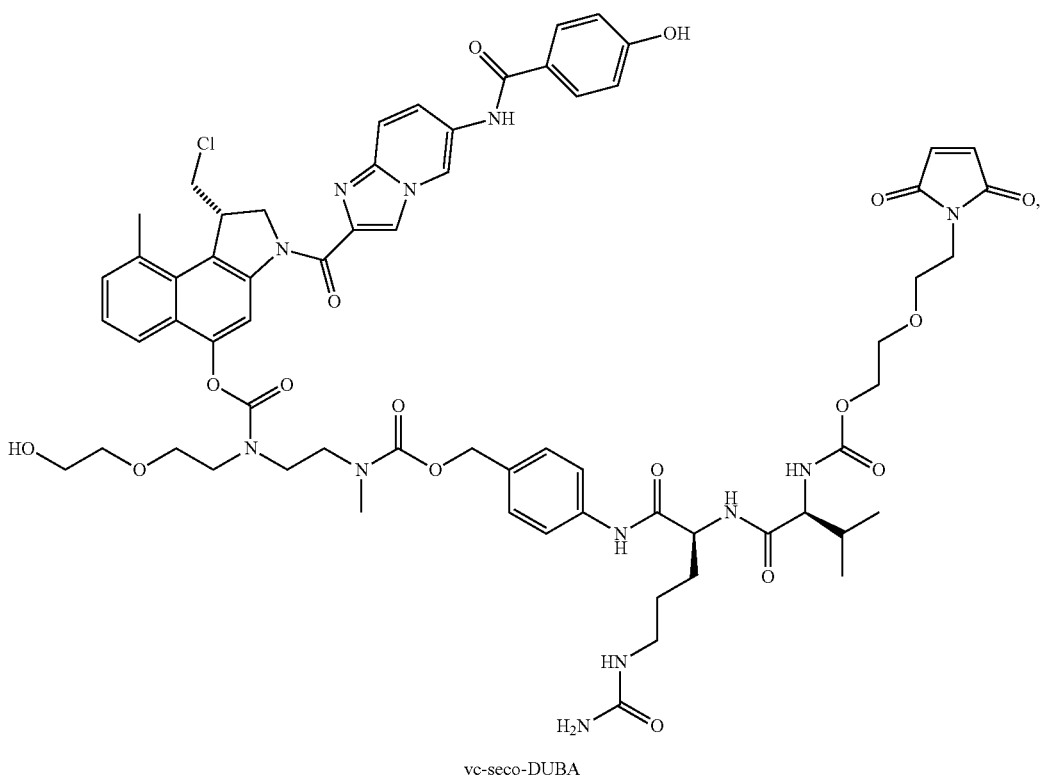

vc-seco-DUBA

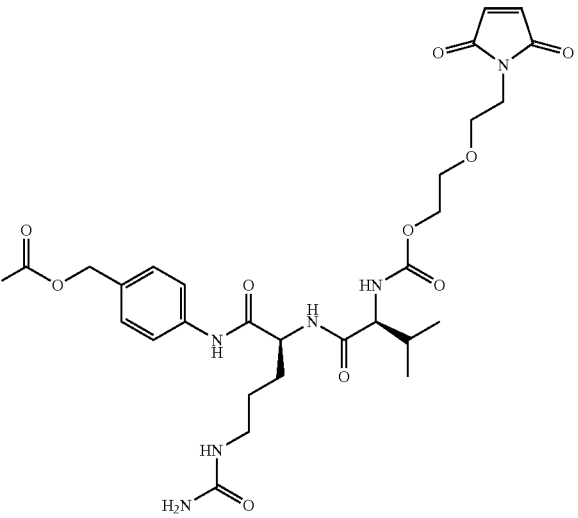

wherein PNP-Cl is 4-nitrophenyl chloroformate, $Et_3N$ is triethylamine, Boc is tert-butyloxycarbonyl, TFA is trifluoroacetic acid, $CHCl_3$ is chloroform, and DMF is N,N-dimethylformamide.

On a 50-100 mg laboratory scale, this four-step process shows an overall yield of only 21-25%. On an industrial scale this yield will be significantly lower.

The low overall yield of this four-step process may for a large part be attributed to the low combined yield of only about 50% on a laboratory scale of the latter two steps, i.e. steps 3 and 4. The present inventors surprisingly found that a modified procedure, involving changing the acid reagent in step 3, yielded a new intermediate which could be isolated via crystallisation. Unexpectedly, it was found that this modified procedure of step 3 and the use of the new intermediate resulted in a considerably increased yield of vc-seco-DUBA.

Typically, a crystallisation step is introduced in a chemical synthesis when the purity of the product needs to be increased. However, the introduction of such step usually reduces the yield of said product, as a considerable amount of product remains in the mother liquor. Surprisingly, the present inventors found that introducing a crystallisation step in the synthesis of vc-seco-DUBA as described hereinabove, leading to the new intermediate of formula (II)

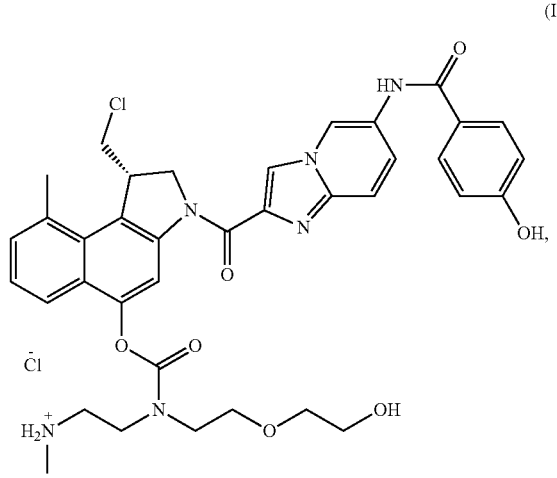

(II)

not only led to an increase in purity (from 94-96% to ≥99.0%), but also showed an unexpected, significant increase in the yield of vc-seco-DUBA (from 53% to ~79%).

Therefore, in one embodiment, the present invention relates to a compound of formula (II).

In a second embodiment, the present invention relates to a process for making a compound of formula (II) comprising reacting a compound of formula (III)

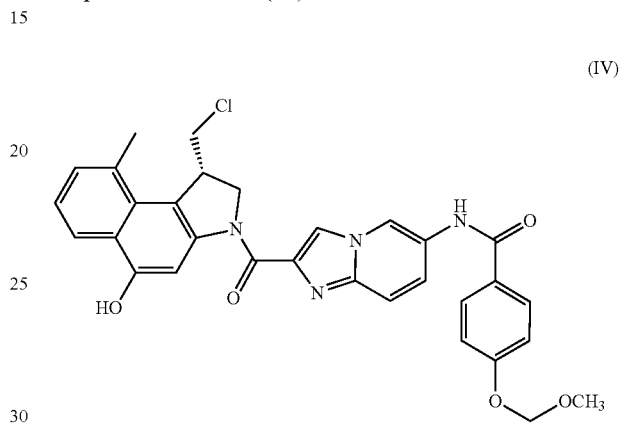

(III)

with hydrogen chloride in 1,4-dioxane to form the compound of formula (II). Typically, the compound of formula (III) is reacted with 10-20 mass % hydrogen chloride in 1,4-dioxane. Preferably, the compound of formula (III) is reacted with 12-18% hydrogen chloride in 1,4-dioxane, more preferably with 15% hydrogen chloride in 1,4-dioxane. Typically, the mass ratio of the compound of formula (III):HCl in 1,4-dioxane ranges of from 1:0.5 to 1:25. Preferably, the mass ratio of the compound of formula (III):HCl in 1,4-dioxane ranges of from 1:1 to 1:10. More preferably of from 1:5 to 1:10.

Typically, the amount of hydrogen chloride is in molar excess of the amount of the compound of formula (III). Preferably, the amount of hydrogen chloride is at least 2 molar equivalents of the amount of the compound of formula (III), more preferably of from 2 to 50 equivalents.

Preferably, said reaction takes place in the presence of a scavenger, such as triisopropylsilane in water and/or methanol. Said water and/or methanol may be present in an amount less than 25 mass % of total solvent mass, preferably less than 15%, more preferably less than 10%.

The compound of formula (III) may be prepared, as described in for example R. C. Elgersma et al., Molecular Cancer Therapeutics, 2015, 12(6), 1813-1835, by reacting a compound of formula (IV)

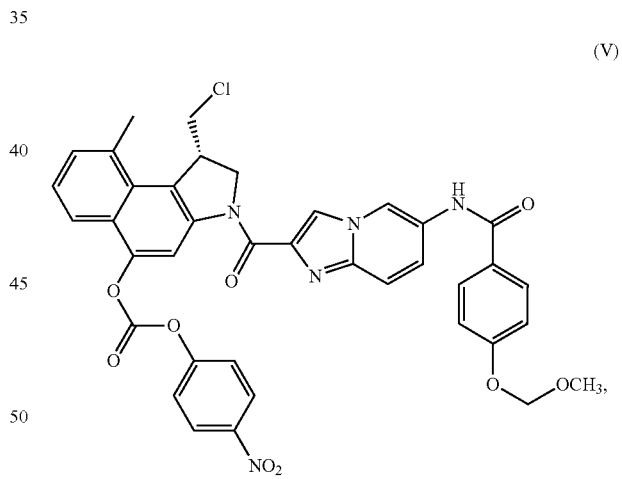

(IV)

with 4-nitrophenyl chloroformate to form a compound of formula (V)

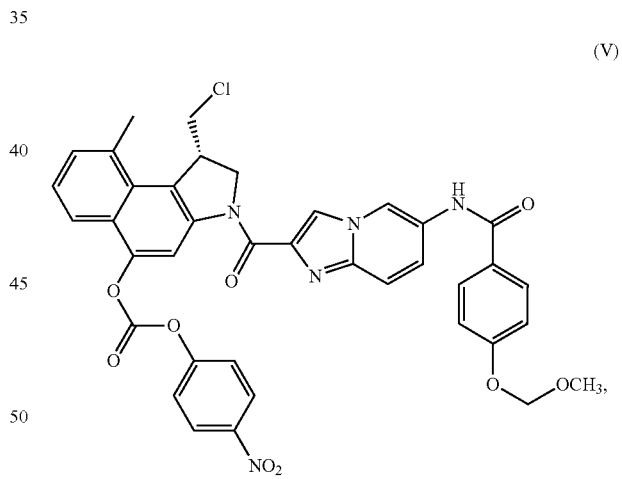

(V)

followed by reacting the compound of formula (V) with a compound of formula (VI)

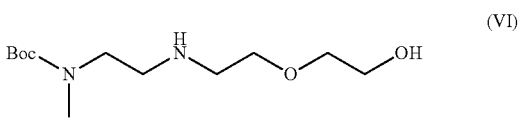 [SMILES: CN(CCNCCOCCO)C(=O)OC(C)(C)C]

(VI)

in the presence of 1-hydroxybenzotriazole hydrate to form the compound of formula (III).

Typically, the reaction of the compound of formula (IV) with 4-nitrophenyl chloroformate is performed at a temperature of from 0 to 20° C. Preferably, the temperature is of from 0 to 10° C., more preferably of from 0 to 6° C., even more preferably of from 2 to 6° C., most preferably of from 3 to 5° C.

Suitable solvents for use in the preparation of the compound of formula (V) are, without limitation, organic solvents, preferably aprotic solvents, more preferably polar aprotic solvents. Preferred solvents are ether solvents, amide solvents or mixtures thereof. Particularly preferred solvents are tetrahydrofuran (THF), N,N-dimethylacetamide (DMA) or mixtures thereof. Most preferred is a mixture of THF and DMA.

Suitable bases for use in the preparation of the compound of formula (V) are organic bases, for example tertiary amines. A particularly suitable base is $Et_3N$.

Typically, the reaction of the compound of formula (V) with the compound of formula (VI) is performed at a temperature of from 0 to 20° C. Preferably, the temperature is of from 0 to 10° C., more preferably of from 4 to 10° C.

Suitable solvents for use in the preparation of the compound of formula (III) are, without limitation, organic solvents, preferably aprotic solvents, polar solvents or mixtures thereof. Preferred solvents are ether solvents, amide solvents or mixtures thereof. Particularly preferred solvents are THF, DMA or mixtures thereof. Most preferred is a mixture of THF and DMA.

The compound of formula (IV) may be produced by, or analogous to, any suitable process known in the prior art, e.g. the process described in Example 6a of WO2015/185142.

In another embodiment, the present invention relates to the use of a compound of formula (II) for making vc-seco-DUBA.

In yet another embodiment, the present invention relates to a process for making vc-seco-DUBA in which a compound of formula (II) is reacted with a compound of formula (VII)

Unexpectedly, the yield of vc-seco-DUBA was even further increased when the compound of formula (II) was reacted with the compound of formula (VII) using N,N-diisopropylethylamine (DIPEA) as the base instead of triethylamine ($Et_3N$), which was used in Example 10 of WO2011/133039. Typically, the molar ratio of the compound of formula (II):DIPEA ranges of from 1:1 to 1:15. Preferably, the ratio ranges of from 1:1 to 1:10, more preferably of from 1:2 to 1:7, even more preferably of from 1:3 to 1:5, most preferably the ratio is about 1:4.

Typically, the reaction of the compound of formula (II) with the compound of formula (VII) is performed at a temperature of from 0 to 20° C. Preferably, the temperature is of from 0 to 10° C., more preferably of from 0 to 5° C.

Suitable solvents for use in the reaction of formula (II) with the compound of formula (VII) to prepare vc-seco-DUBA are, without limitation, organic solvents, preferably aprotic solvents, more preferably polar aprotic solvents. Preferred solvents are ether solvents, amide solvents or mixtures thereof. Particularly preferred solvents are THF, DMA, N,N-dimethylformamide (DMF) or mixtures thereof. Most preferred is DMA.

In a preferred embodiment, the process is performed in the presence of 1-hydroxybenzotriazole hydrate. Typically, the molar ratio of the compound of formula (II):1-hydroxybenzotriazole hydrate ranges of from 1:1 to 1:10. Preferably, the ratio ranges of from 1:1 to 1:7, more preferably of from 1:2 to 1:5, even more preferably of from 1:2 to 1:3, most preferably the ratio is about 1:2.5.

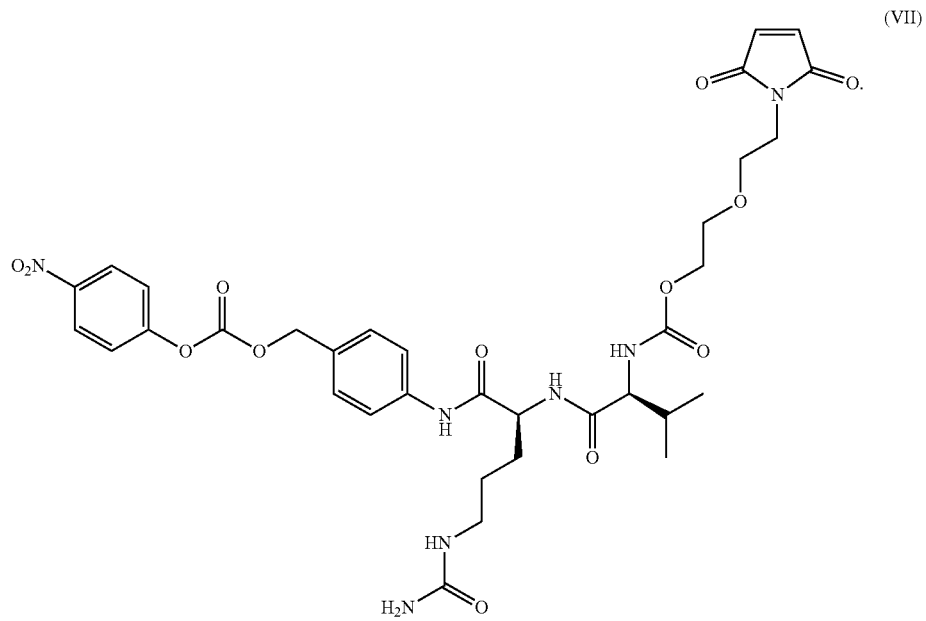 [SMILES: CC(C)[C@H](NC(=O)OCCOCCN1C(=O)C=CC1=O)C(=O)N[C@@H](CCCNC(N)=O)C(=O)Nc1ccc(COC(=O)Oc2ccc([N+](=O)[O-])cc2)cc1]

The present invention additionally relates to a process for the preparation of a vc-seco-DUBA ADC of formula (VIII)

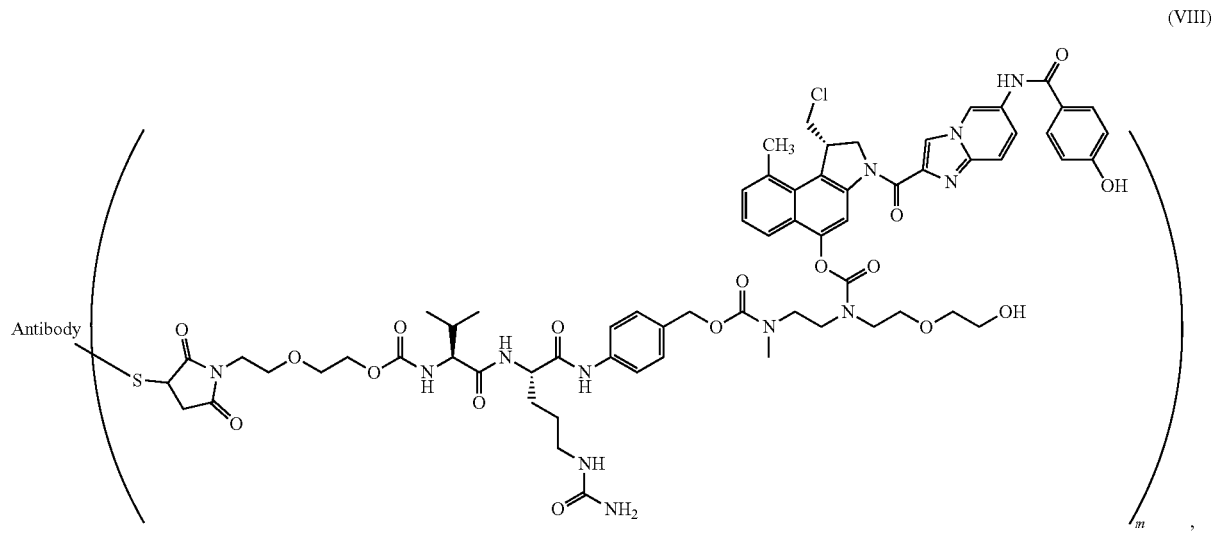

wherein the vc-seco-DUBA linker-drug compound is prepared with the process according to the invention as described hereinabove.

In represents an average drug-to-antibody ratio (DAR) of from 1 to 8, preferably of from 1 to 6, more preferably of from 1 to 4.

In the context of the present invention, any antibody—particularly any antibody known to have therapeutic activity or any antibody known in the art of ADCs—or any antigen-binding fragment thereof, e.g. a F(ab')$_2$ or a Fab' fragment, a single chain (sc) antibody, a scFv, a single domain (sd) antibody, a diabody, or a minibody, can be used for (wild-type or site-specific) conjugation of vc-seco-DUBA. Antibodies may be of any isotype such as IgG, IgA or IgM antibodies. Preferably, the antibody is an IgG antibody, more preferably an IgG$_1$ or IgG$_2$ antibody. The antibodies may be chimeric, humanized or human. Preferably, the antibodies are humanized. Even more preferably, the antibody is a humanized or human IgG antibody, most preferably a humanized or human IgG$_1$ monoclonal antibody (mAb). Preferably, said antibody has κ (kappa) light chains, i.e., a humanized or human IgG$_1$-κ antibody.

In humanized antibodies, the antigen-binding complementarity determining regions (CDRs) in the variable regions of the heavy chain (HC) and light chain (LC) are derived from antibodies from a non-human species, commonly mouse, rat or rabbit. These non-human CDRs may be placed within a human framework (framework region (FR) FR1, FR2, FR3 and FR4) of the variable regions of the HC and LC. Selected amino acids in the human FRs may be exchanged for the corresponding original non-human species amino acids, e.g. to improve binding affinity, while retaining low immunogenicity. Alternatively, the non-human frameworks are retained and selected amino acids of the non-human species FRs may be exchanged for their corresponding human amino acids to reduce immunogenicity, while retaining the antibody's binding affinity. The thus humanized variable regions are combined with human constant regions.

These antibodies may be produced recombinantly, synthetically, or by other suitable methods known in the art.

Typically, the antibody is a monospecific (i.e. specific for one antigen; such antigen may be common between species or have similar amino acid sequences between species) or bispecific (i.e. specific for two different antigens of a species) antibody comprising at least one HC and LC variable region binding to a target selected from the group consisting of annexin A1, B7H4, CA6, CA9, CA15-3, CA19-9, CA27-29, CA125, CA242 (cancer antigen 242), CCR2, CCR5, CD2, CD19, CD20, CD22, CD30 (tumour necrosis factor 8), CD33, CD37, CD38 (cyclic ADP ribose hydrolase), CD40, CD44, CD47 (integrin associated protein), CD56 (neural cell adhesion molecule), CD70, CD74, CD79, CD115 (colony stimulating factor 1 receptor), CD123 (interleukin-3 receptor), CD138 (Syndecan 1), CD203c (ENPP3), CD303, CD333, CEA, CEACAM, CLCA-1 (C-type lectin-like molecule-1), CLL-1, c-MET (hepatocyte growth factor receptor), Cripto, DLL3, EGFL, EGFR, EPCAM, EPh (e.g. EphA2 or EphB3), ETBR (endothelin type B receptor), FAP, FcRL5 (Fc receptor-like protein 5, CD307), FGFR (e.g. FGFR3), FOLR1 (folate receptor alpha), GCC (guanylyl cyclase C), GPNMB, HER2, HMW-MAA (high molecular weight melanoma-associated antigen), integrin α (e.g. αvβ3 and αvβ5), IGF1R, TM4SF1(or L6 antigen), Lewis A like carbohydrate, Lewis X, Lewis Y (CD174), LIV1, mesothelin (MSLN), MN (CA9), MUC1, MUC16, NaPi2b, Nectin-4, PD-1, PD-L1, PSMA, PTK7, SLC44A4, STEAP-1, 5T4 antigen (or TPBG, trophoblast glycoprotein), TF (tissue factor, thromboplastin, CD142), TF-Ag, Tag72, TNFR, TROP2 (tumour-associated calcium signal transducer 2), VEGFR and VLA.

Examples of suitable antibodies include blinatumomab (CD19), epratuzumab (CD22), iratumumab and brentuximab (CD30), vadastuximab (CD33), tetulumab (CD37), isatuximab (CD38), bivatuzumab (CD44), lorvotuzumab (CD56), vorsetuzumab (CD70), milatuzumab (CD74), polatuzumab (CD79), rovalpituzumab (DLL3), futuximab (EGFR), oportuzumab (EPCAM), farletuzumab (FOLR1), glembatumumab (GPNMB), trastuzumab and pertuzumab (HER2), etaracizumab (integrin), anetumab (mesothelin), pankomab (MUC1), enfortumab (Nectin-4), and H8, A1, and A3 (5T4 antigen).

Conjugation of the vc-seco-DUBA linker-drug to the antibody may be performed as described for example in WO2011/133039, WO2015/177360 and WO2017/137628.

Wild-type ADCs are produced by conjugating the linker-drug to the antibody through the free thiols of the side chains of cysteines generated through reduction of interchain disulfide bonds. The manufacture involves partial reduction of the solvent-exposed interchain disulfides followed by modification of the resulting thiols with maleimide-containing linker-drugs. The cysteine attachment strategy results in maximally two drugs per reduced disulfide. Most human IgG molecules have four solvent-exposed disulfide bonds, and so a range of from zero to eight drugs per antibody is possible. The exact number of drugs per antibody is determined by the extent of disulfide reduction and the number of molar equivalents of linker-drug used in the ensuing conjugation reaction. Full reduction of all four disulfide bonds gives a homogeneous construct with eight drugs per antibody, while a partial reduction typically results in a heterogeneous mixture with zero, two, four, six, or eight drugs per antibody.

Site-specific ADCs are produced by conjugating the linker-drug to the antibody through the side chains of engineered cysteine residues in suitable positions of the mutated antibody. Engineered cysteines are usually capped by other thiols, such as cysteine or glutathione, to form disulfides. These capped residues need to be uncapped before drug attachment can occur. Drug attachment to the engineered residues is either achieved by reducing both the native interchain and mutant disulfides, then re-oxidizing the native interchain cysteines using a mild oxidant such as $CuSO_4$ or dehydroascorbic acid, followed by standard conjugation of the uncapped engineered cysteine with a linker-drug, or by using mild reducing agents which reduce mutant disulfides at a higher rate than the interchain disulfide bonds, followed by standard conjugation of the uncapped engineered cysteine with a linker-drug. Under optimal conditions, two drugs per antibody (i.e. drug-to-antibody ratio, DAR, is 2) will be attached (if one cysteine is engineered into the heavy chain or light chain of the mAb).

In a preferred embodiment, the antibody to be used in accordance with the present invention is an anti-HER2 antibody, even more preferred the anti-HER2 antibody trastuzumab.

In one particular embodiment, the present invention relates to a process for the preparation of a trastuzumab vc-seco-DUBA ADC of formula (IX)

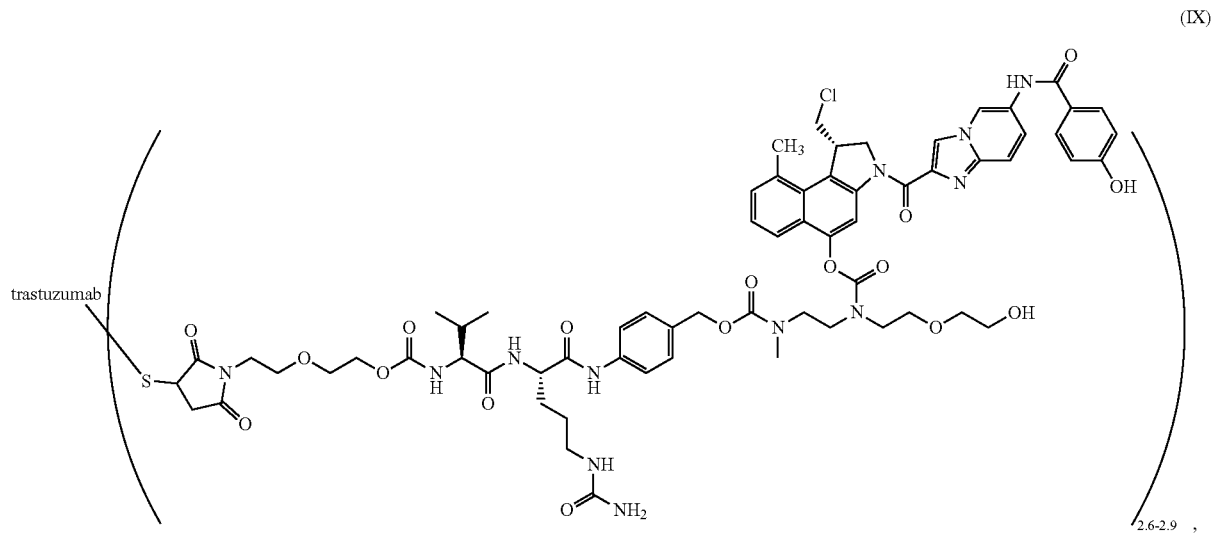

(IX)

wherein the vc-seco-DUBA linker-drug compound is prepared with the process according to the invention as described hereinabove. 2.6-2.9 represents an average DAR of from 2.6-2.9.

EXAMPLES

Example 1 - Preparation of methylCBI-azaindole-benzamide-MOM—Boc-ethylenediamine-D (4)

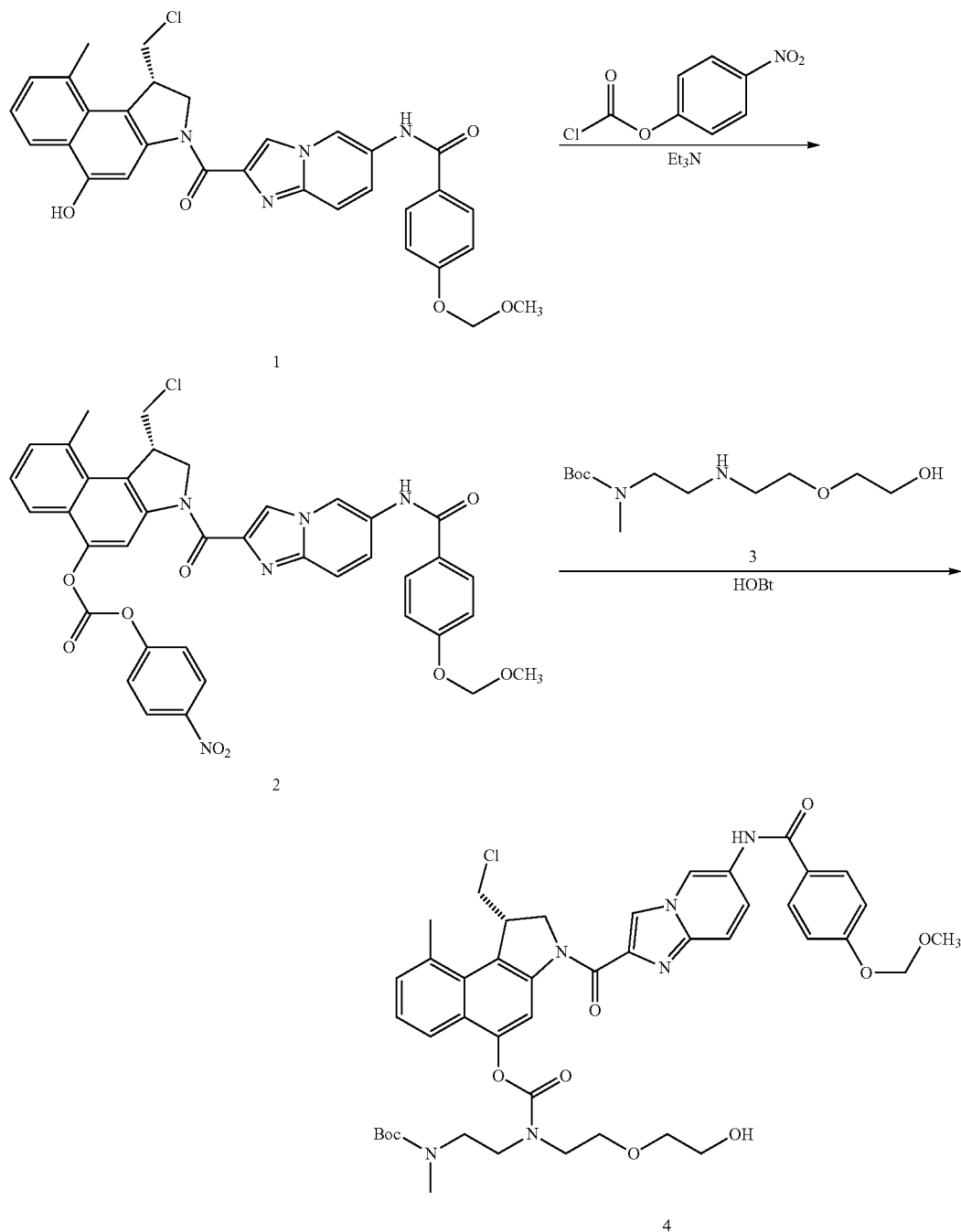

MethylCBI-azaindole-benzamide-MOM (1) (1.0 g, 1.75 mmol) was reacted with 4-nitrophenyl chloroformate (PNP-Cl) (0.43 g, 2.12 mmol) in a mixture of tetrahydrofuran (THF) (4.5 g) and N,N-dimethylacetamide (DMA) (3.0 g) in the presence of triethylamine (Et$_3$N) (0.55 g, 4.94 mmol) for about 1.5 hrs at a temperature of 0° C. allowed to warm up to 6° C. A slurry comprising methylCBI-azaindole-benzamide-MOM-PNP (2) was obtained.

In the second step, tert-butyl (2-((2-(2-hydroxyethoxy)ethyl)amino)ethyl)(methyl)-carbamate (3) (0.58 g, 2.19 mmol) was dissolved in DMA (1.7 g) and 1-hydroxybenzotriazole hydrate (HOBt) (0.35 g, 2.28 mmol) was added. This obtained solution was reacted with the slurry for 1.5 hrs at a temperature of 4° C. allowed to warm up to 10° C.

After completion of the reaction, ethyl acetate (EtOAc) (8.8 g) was added to the reaction mixture and the solution was washed with brine (11.3 g), saturated sodium bicarbonate solution (3.8 g) and again with brine (3.8 g). The organic layer was separated and purified by carbon filtration. The solvent was evaporated on a rotary vacuum evaporator. The obtained methylCBI-azaindole-benzamide-MOM-Boc-ethylenediamine-D (4) was dissolved in acetone (20 g) and, eventually, purified again by carbon filtration.

The crude product was purified by silica gel column chromatography, eluting it with a mobile phase—DCM:MeOH=97:3 to 94:6. The combined product fractions were concentrated and dried in vacuo to yield methylCBI-azaindole-benzamide-MOM-Boc-ethylenediamine-D (4) (1.27 g, 1.48 mmol; 84% yield, 93.82% pure).

The methoxymethyl (MOM) and tert-butyloxycarbonyl (Boc) groups of methylCBI-azaindole-benzamide-MOM-Boc-ethylenediamine-D (4) (1.27 g, 1.48 mmol) were removed by 15% hydrogen chloride (HCl) in 1,4-dioxane (7.5 g) in the presence of a scavenger (triisopropyl silane (0.63 g), water (0.4 g) and methanol (0.3 g)). MethylCBI-azaindole-benzamide-ethylenediamine-D hydrochloride (5) crystallised from the reaction solution as a yellow solid.

The obtained yellow solid was filtered off, washed with acetone and dried on the filter using nitrogen and vacuum providing a pure product (5) (1.0 g, 1.33 mmol; 90% yield, ≥90% purity).

Example 2 - Preparation of vc-seco-DUBA
Preparation of methylCBI-azaindole-benzamide-ethylenediamine-D hydrochloride (5)

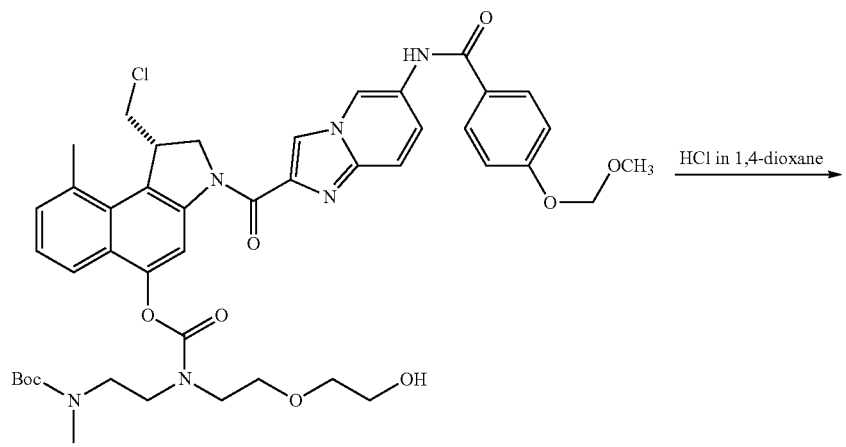

4

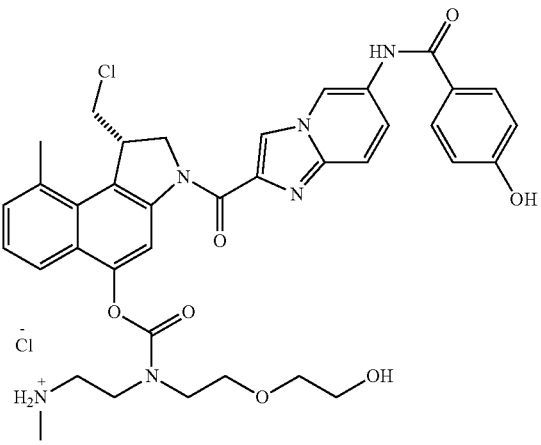

5

Preparation of vc-seco-DUBA

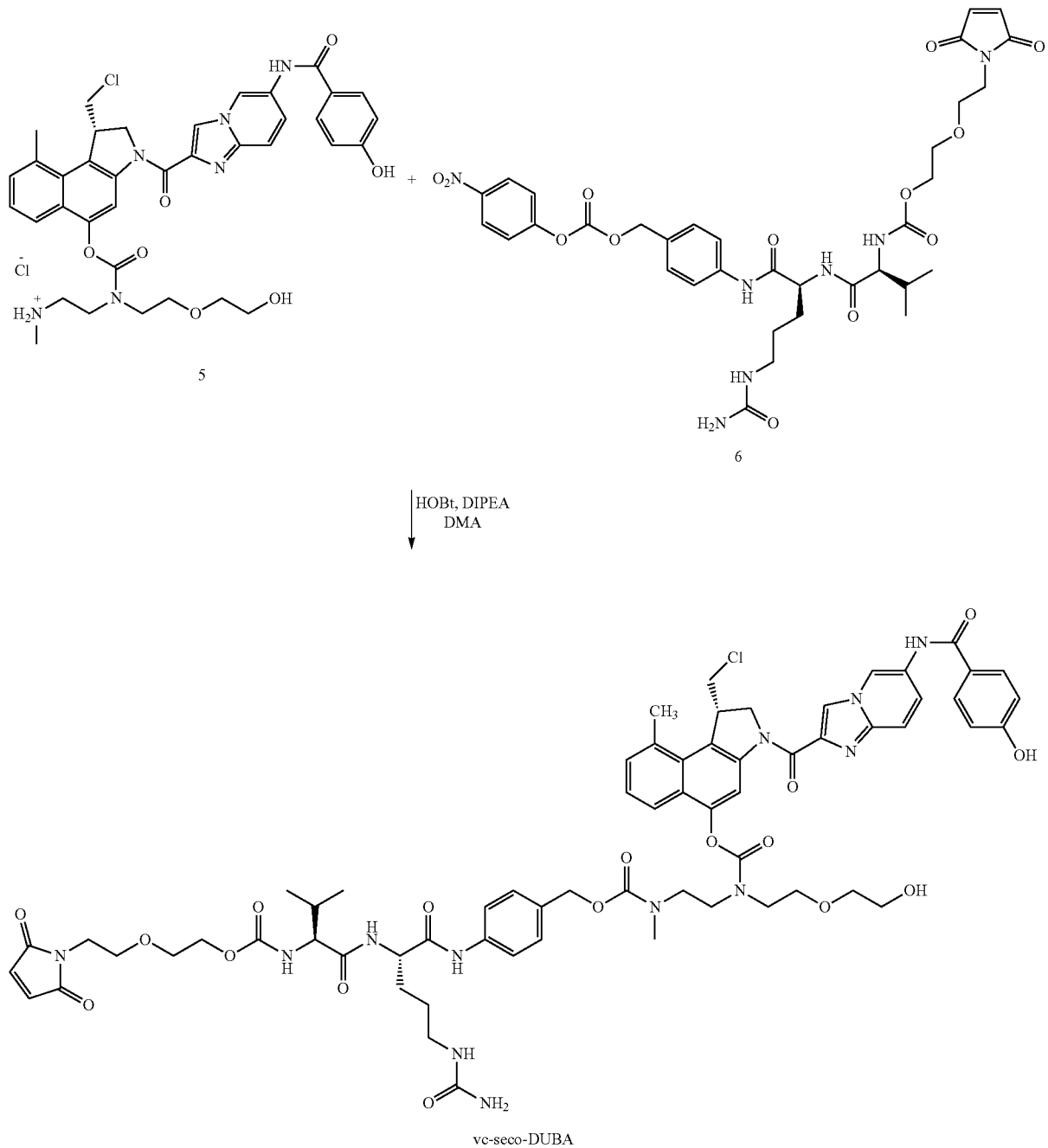

vc-seco-DUBA

MethylCBI-azaindole-benzamide-ethylenediamine-D hydrochloride (5) (1.0 g, 1.33 mmol) was reacted for 1.5 hrs in the dark at a temperature of 0° C. allowed to warm up to 5° C. with maleimide-OEG2-val-cit-PABA-PNP (6) (0.98 g, 1.29 mmol) in DMA (17.8 g) in the presence of N,N-diisopropylethylamine (DIPEA) (0.65 g, 5.10 mmol) and HOBt (0.47 g, 3.16 mmol). The reaction mixture was added dropwise to water (201.1 g) at a temperature of 23 to 25° C. (50 to 60 min) and a precipitate of vc-seco-DUBA crude product was obtained. After 30 min of stirring, the precipitated crude product was filtered in a pressure filter. The filter cake was thoroughly washed with water and dried in the filter under vacuum and slight nitrogen flow.

vc-seco-DUBA crude product was subjected first to low pressure flash chromatography (stationary phase-silica gel 0.040 to 0.063 mm; mobile phase-dichloromethane:methanol=90:10). Complying fractions (with UPLC-IN purity of vc-seco-DUBA≥90%) were collected in a flask, filtered and evaporated. A further purification was performed by preparative chromatography (stationary phase-silica gel 0.015 to 0.040 mm; mobile phase-dichloromethane:methanol=90: 10 to 85:15). Complying fractions (with UPLC-IN purity of vc-seco-DUBA≥90%) were collected in a flask and the solvent was switched to DMA. Concentration was performed at a maximum temperature of 25° C. Concentrated solutions were combined, filtered via a 0.2 μm filter and added to water to precipitate pure vc-seco-DUBA as a fine yellow powder (yield: 35-45%; purity: ≥99.0%).

The product was filtered, washed with water and dried in the filter using nitrogen and vacuum at a temperature of maximum 25° C.

COMPARATIVE EXAMPLE

Preparation of vc-seco-DUBA

The synthesis of vc-seco-DUBA is performed following the procedure described in Example 10 of WO2011/133039.

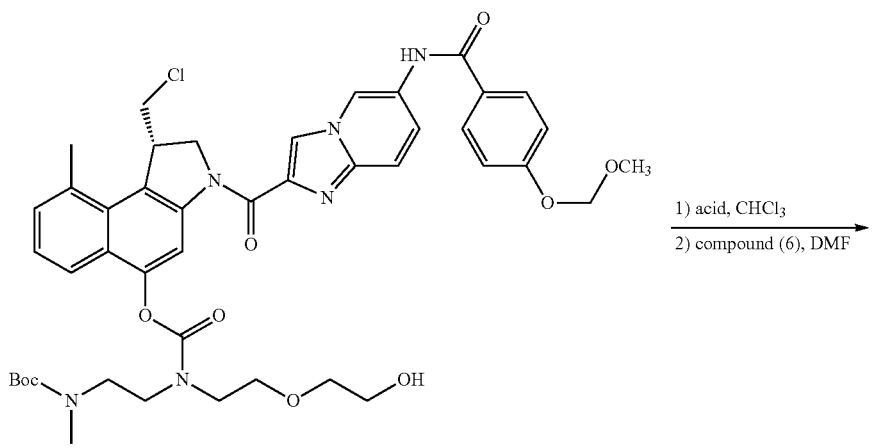

4

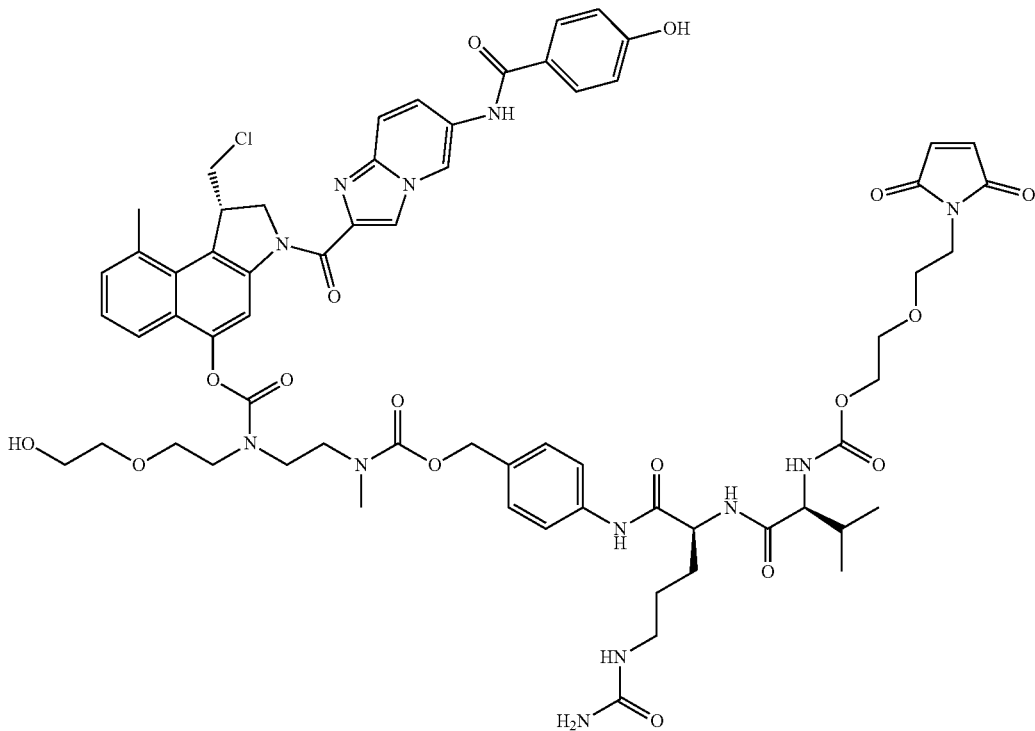

vc-seco-DUBA

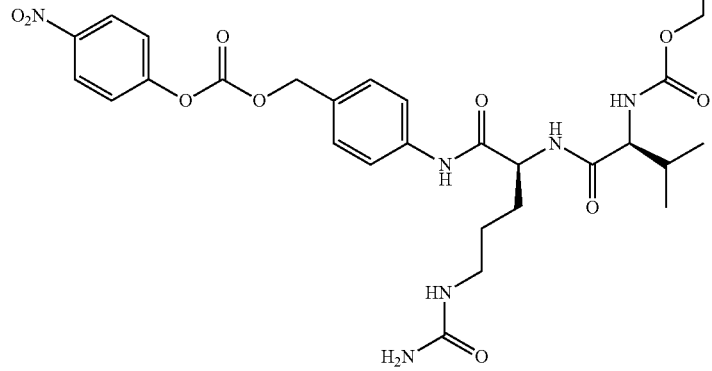

Step 1

MethylCBI-azaindole-benzamide-MOM-Boc-ethylenediamine-D (4) (0.1 mmol) was suspended in chloroform (CHCl$_3$) (6 ml) and cooled in ice. 2 ml of acid (trifluoroacetic acid (TFA) or 15% HCl in 1,4 dioxane (7.5 g)) were added and the mixture was stirred for 3 hrs. The mixture was then concentrated in vacuo.

Step 2

The residue was dissolved in N,N-dimethylformamide (DMF) (4 ml), the solution cooled in ice and maleimide-OEG2-val-cit-PABA-PNP (6) (0.13 mmol) and the base (1 mmol, Et$_3$N or DIPEA) were added. The mixture was stirred for 2 hrs, concentrated in vacuo and the residue purified by column chromatography (SiO$_2$, dichloromethane:methanol, 1:0 to 8:2).

The above procedure was performed using either HCl in 1,4-dioxane or the prior art acid TFA to remove the MOM and Boc groups of methylCBI-azaindole-benzamide-MOM-Boc-ethylenediamine-D (4) in the first step and using either DIPEA or the prior art base Et$_3$N to facilitate the coupling reaction of methylCBI-azaindole-benzamide-ethylenediamine-D hydrochloride (5) and maleimide-OEG2-val-cit-PABA-PNP (6) in step 2 in order to determine the influence of the choice of acid and base on the efficiency of the preparation of vc-seco-DUBA.

The table below shows the yield of vc-seco-DUBA.

| Acid used in Step 1 | Base used in Step 2 | Intermediate (5) isolated | Yield (%) |
|---|---|---|---|
| TFA* | Et$_3$N* | No | 52.96 |
| TFA | DIPEA | No | 29.32 |
| HCl in 1,4-dioxane | Et$_3$N | Yes | 78.76 |
| HCl in 1,4-dioxane | DIPEA | Yes | 82.80 |

*Acid and reagent used in prior art process (WO2011/133039)

The use of HCl in 1,4-dioxane instead of TFA in step 1 resulted in a 25.8% increase in the overall yield of vc-seco-DUBA as determined by HPLC. The use of DIPEA instead of Et$_3$N in step 2 resulted in a 23.6% decrease in the overall yield of vc-seco-DUBA as determined by HPLC. However, the use of HCl in 1,4-dioxane in step 1 and DIPEA in step 2 resulted in a 29.8% increase in the overall yield of vc-seco-DUBA as determined by HPLC.

The invention claimed is:

1. A compound of formula (II):

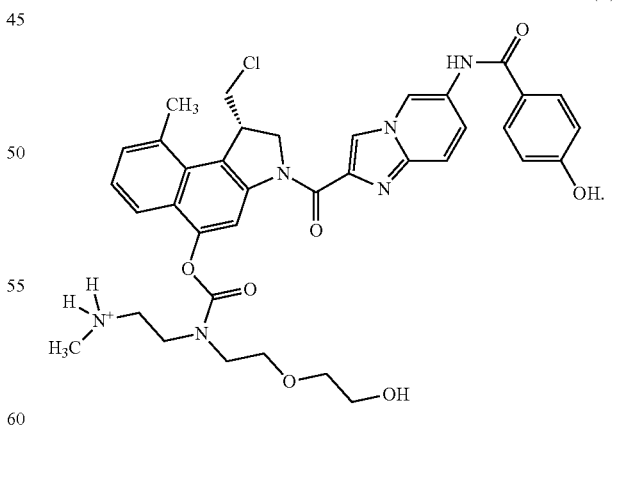

2. The compound according to claim 1, wherein the compound is in solid form.

3. The compound according to claim 2, wherein the solid form is a crystalline solid form.

4. A process for the synthesis of a compound of formula (II):
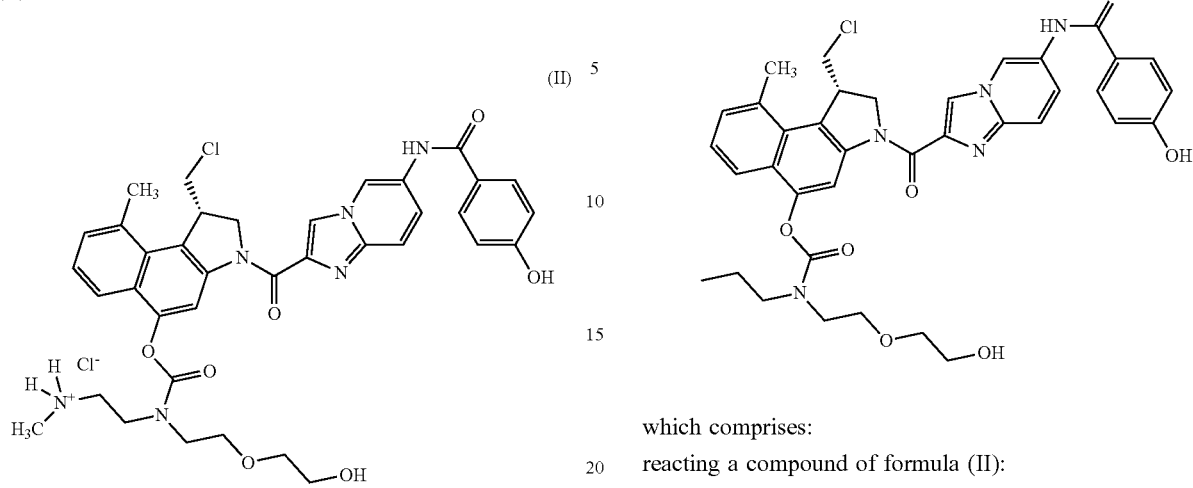
which comprises reacting a compound of formula (III):
with hydrogen chloride in 1,4-dioxane to form the compound of formula (II).
5. A process for the synthesis of vc-seco-DUBA of formula (I):
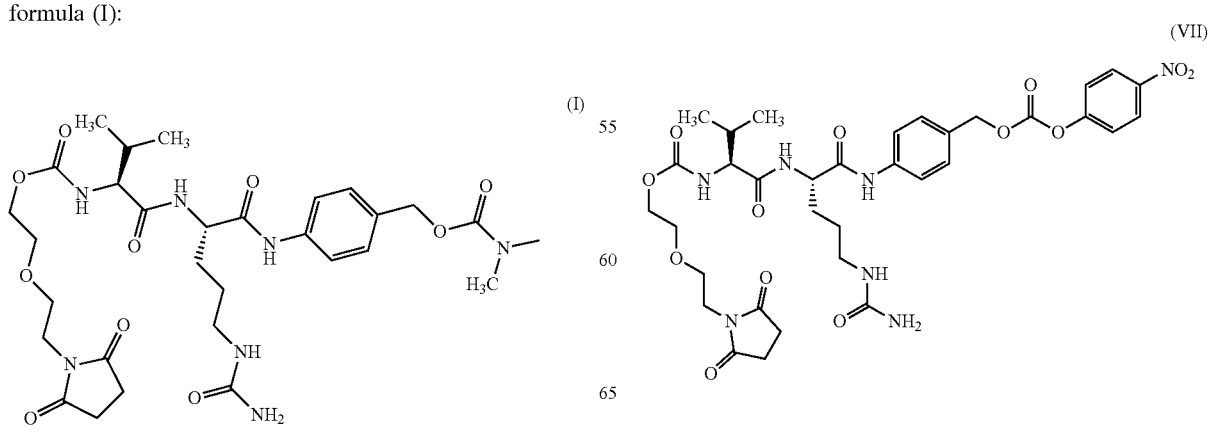
-continued
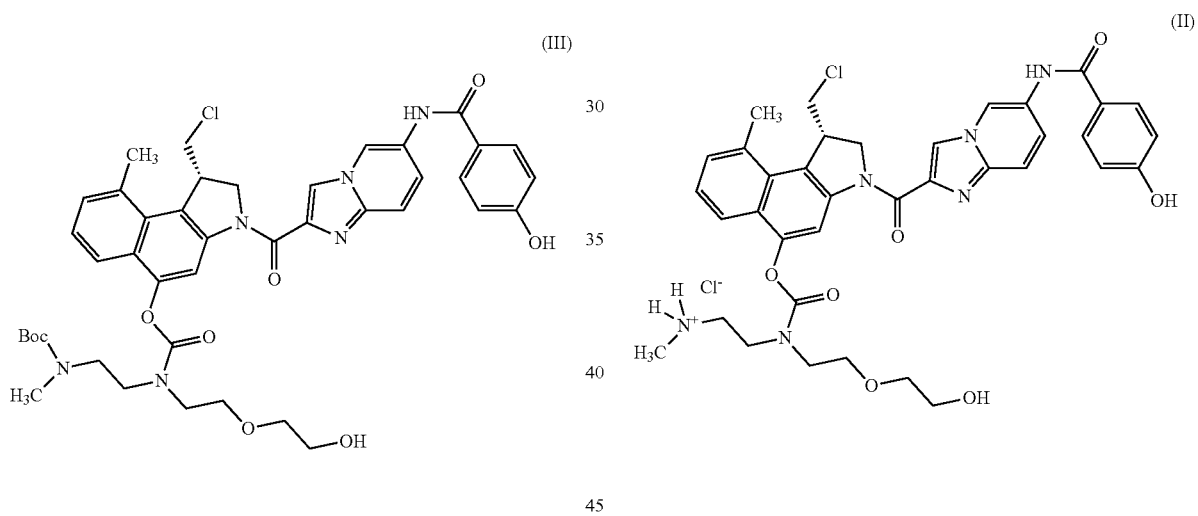
which comprises:
reacting a compound of formula (II):
with a compound of formula (VII):
to form vc-seco-DUBA of formula (I).

6. The process according to claim 5, wherein the reaction of the compound of formula (II) with the compound of formula (VII) is performed in the presence of N,N-diisopropylethylamine.

7. The process according to claim 5, wherein the reaction of the compound of formula (II) with the compound of formula (VII) is performed in N,N-dimethylacetamide in the presence of N,N-diisopropylethylamine and 1-hydroxybenzotriazole hydrate.

8. The process according to claim 5, which further comprises forming the compound of formula (II) by reacting a compound of formula (III):

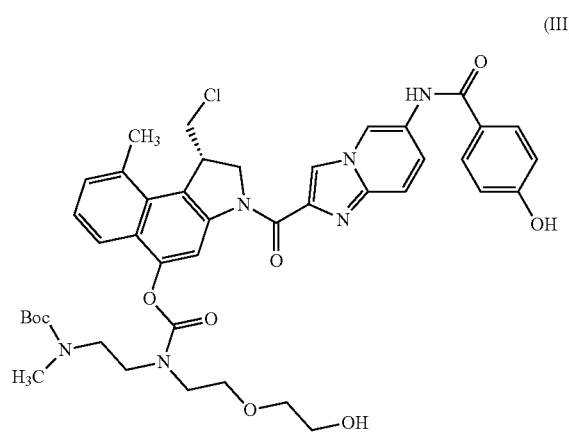 [SMILES: Cc1cccc2c(OC(=O)N(CCOCCO)CCN(C)C(=O)OC(C)(C)C)cc3c(c12)[C@H](CCl)CN3C(=O)c1cn2cc(NC(=O)c3ccc(O)cc3)ccc2n1]

(III)

with hydrogen chloride in 1,4-dioxane to form the compound of formula (II).

9. The process according to claim 8, which further comprises isolating the compound of formula (II) via crystallization.

10. The process according to claim 8, which further comprises forming the compound of formula (III) by reacting a compound of formula (IV):

(IV)

with 4-nitrophenyl chloroformate to form a compound of formula (V):

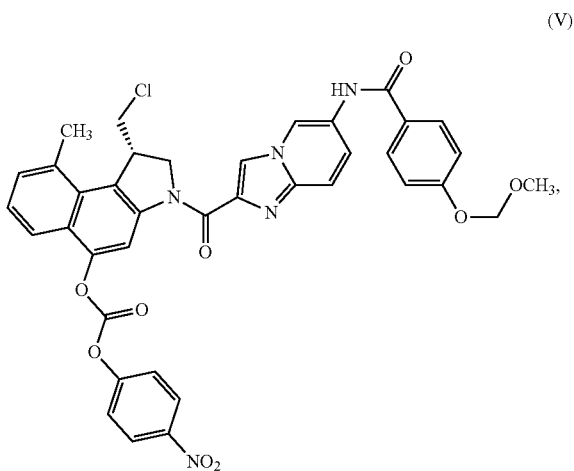 [SMILES: COCOc1ccc(C(=O)Nc2ccc3nc(C(=O)N4C[C@@H](CCl)c5c4cc(OC(=O)Oc4ccc([N+](=O)[O-])cc4)c4cccc(C)c54)cn3c2)cc1]

(V)

followed by reacting the compound of formula (V) with a compound of formula (VI):

(VI)

in the presence of 1-hydroxybenzotriazole hydrate to form the compound of formula (III).

11. A process for the synthesis of an antibody-drug conjugate of formula (VIII):

(VIII)

wherein:
Antibody is an antibody or an antigen-binding fragment thereof; and
m is an average drug-to-antibody ratio of from 1 to 8;
which comprises:
(1) reacting a compound of formula (II):

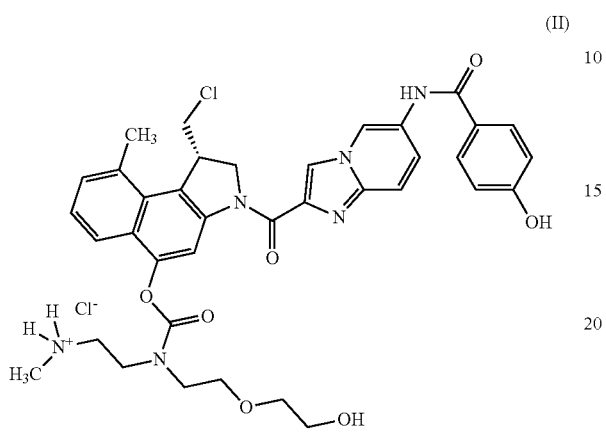

with a compound of formula (VII):

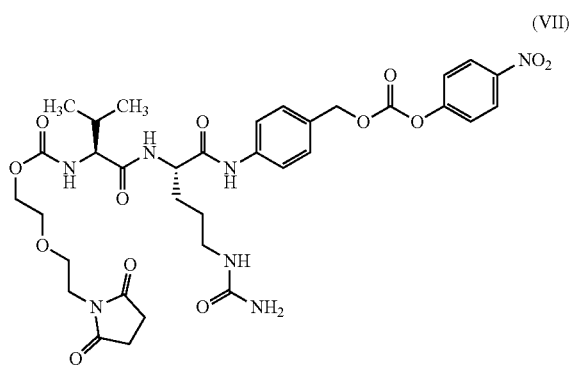 [SMILES: CC(C)[C@H](NC(=O)OCCOCCN1C(=O)CCC1=O)C(=O)N[C@@H](CCCNC(N)=O)C(=O)Nc1ccc(COC(=O)Oc2ccc([N+](=O)[O-])cc2)cc1]

to form vc-seco-DUBA of formula (I):

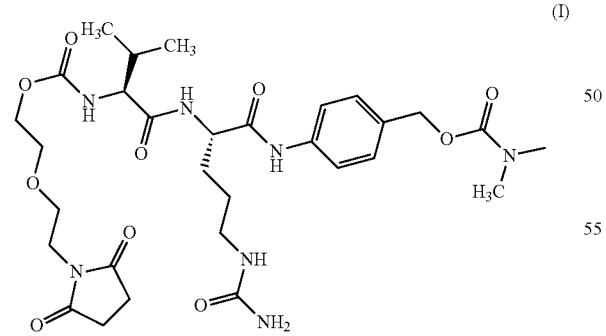

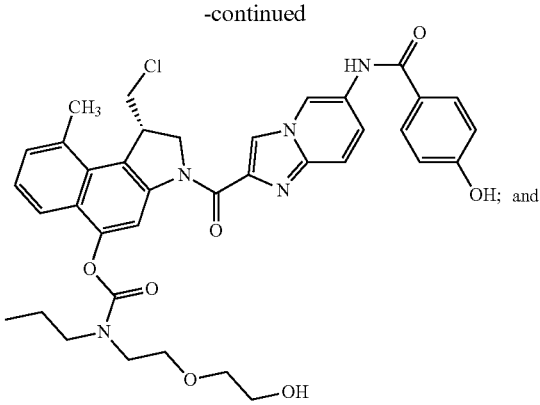

(2) conjugating vc-seco-DUBA of formula (I) to an antibody, or an antigen-binding fragment thereof, to form an antibody-drug conjugate of formula (VIII).

12. The process according to claim 11, wherein m is an average drug-to-antibody ratio of from 1 to 6.

13. The process according to claim 11, wherein m is an average drug-to-antibody ratio of from 1 to 4.

14. The process according to claim 11, wherein vc-seco-DUBA of formula (I) is conjugated to an anti-HER2 antibody.

15. The process according to claim 14, wherein the antibody is trastuzumab.

16. The process according to claim 15, wherein the formed antibody-drug conjugate is of formula (IX):

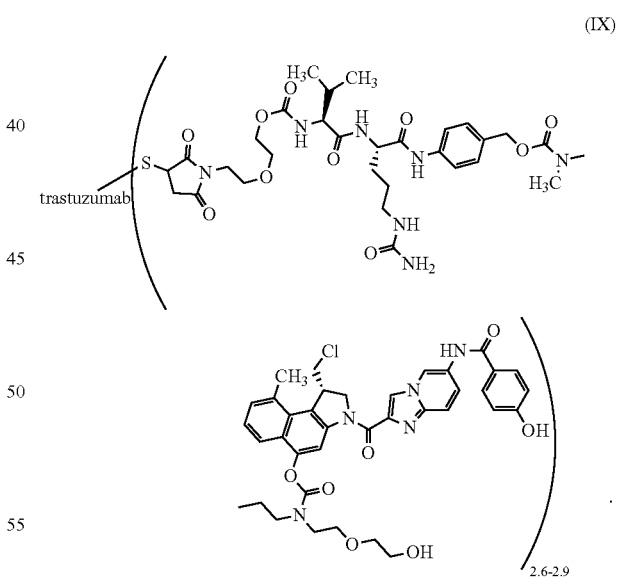

* * * * *